(12) United States Patent
Hachiya et al.

(10) Patent No.: US 6,277,945 B1
(45) Date of Patent: Aug. 21, 2001

(54) METHOD FOR PRODUCING AN AROMATIC POLYCARBONATE

(75) Inventors: Hiroshi Hachiya; Kyosuke Komiya, both of Kurashiki (JP)

(73) Assignee: Asahi Kasei Kogyo Kabushiki Kaisha, Osaka (JP)

( * ) Notice: Subject to any disclaimer, the term of this patent is extended or adjusted under 35 U.S.C. 154(b) by 0 days.

(21) Appl. No.: 09/368,362

(22) Filed: Aug. 5, 1999

(30) Foreign Application Priority Data

Aug. 5, 1998 (JP) .................................................. 10-221656

(51) Int. Cl.$^7$ .................................................. C08G 64/00
(52) U.S. Cl. ............................................. 528/196; 528/198
(58) Field of Search ..................................... 528/196, 198

(56) References Cited

U.S. PATENT DOCUMENTS 5,747,609  5/1998  Komiya et al. ..................... 526/68

FOREIGN PATENT DOCUMENTS 10060106A  3/1998  (JP) .

Primary Examiner—Terressa M. Boykin
(74) Attorney, Agent, or Firm—Birch, Stewart, Kolasch & Birch, LLP

(57) ABSTRACT

Disclosed is a method for producing an aromatic polycarbonate, which comprises reacting acetone with a phenol material, thereby producing bisphenol A, and polymerizing the resultant bisphenol A with diphenyl carbonate to produce an aromatic polycarbonate while producing phenol as a by-product, wherein the by-product phenol is recovered as a crude phenol product containing the by-product phenol as a main component and containing impurities, and the crude phenol product is used as at least a part of the phenol material for producing bisphenol A. According to the method of the present invention, a crude phenol product as such, containing, as a main component, a by-product phenol which is by-produced during the polymerization reaction for producing an aromatic polycarbonate, and containing impurities, can be utilized for producing an aromatic polycarbonate, without any purification or the like. In the method of the present invention, not only can a necessity for complicated operations, such as a purification treatment, be reduced, but also the amount of wastes can be reduced and the yield of the aromatic polycarbonate, based on any of phenol and bisphenol A, can be improved.

6 Claims, 7 Drawing Sheets

METHOD FOR PRODUCING AN AROMATIC POLYCARBONATE

BACKGROUND OF THE INVENTION

1. Field of the Invention

The present invention relates to a method for producing an aromatic polycarbonate. More particularly, the present invention is concerned with a method for producing an aromatic polycarbonate, which comprises: reacting acetone with a phenol material to produce bisphenol A, and polymerizing the bisphenol A with diphenyl carbonate to produce an aromatic polycarbonate while producing phenol as a by-product, wherein the by-product phenol is recovered as a crude phenol product containing the by-product phenol as a main component and containing impurities, and the crude phenol product is used as at least a part of the phenol material for producing bisphenol A. According to the method of the present invention, a crude phenol product as such, containing, as a main component, by-product phenol (occurring during the polymerization reaction for producing an aromatic polycarbonate) and containing impurities, can be utilized for producing bisphenol A, finally for producing an aromatic polycarbonate, without any purification or the like. Therefore, in the method of the present invention, not only can a necessity for complicated operations, such as a purification treatment, be reduced, but also the amount of wastes can be reduced and the yield of the aromatic polycarbonate, based on any of phenol and bisphenol A, can be improved.

2. Prior Art

In recent years, aromatic polycarbonates have been widely used in various fields as engineering plastics having excellent heat resistance, impact resistance and transparency.

With respect to methods for producing aromatic polycarbonates, various studies have heretofore been made. Of the methods studied, a process utilizing an interfacial polycondensation between an aromatic dihydroxy compound, such as bisphenol A {2,2-bis(4-hydroxyphenyl) propane} and phosgene, has been commercially practiced. However, the interfacial polycondensation process has problems in that it is necessary to use phosgene, which is poisonous, that a reaction apparatus is likely to be corroded with chlorine-containing compounds, such as hydrogen chloride and sodium chloride, which are by-produced, and methylene chloride which is used as a solvent in a large quantity, and that difficulties are encountered in separating and removing impurities, such as sodium chloride, and residual methylene chloride, which adversely affect properties of a produced polymer.

For solving the above-mentioned problems, various methods for producing an aromatic polycarbonate by a transesterification process by using a diaryl carbonate instead of phosgene have been proposed. For example, an aromatic polycarbonate can be produced by polymerizing bisphenol A with diphenyl carbonate (DPC) in molten state. In this method, a high polymerization degree of the polycarbonate cannot be achieved without distilling off an aromatic monohydroxy compound (such as phenol) produced as a by-product from the highly viscous molten polycarbonate. Therefore, this method has various disadvantages in the following points: (1) since a high temperature is needed for the polymerization, branching and/or crosslinking are likely to occur as side reactions, so that it is difficult to obtain a high quality polycarbonate; (2) undesirable discoloration of the polymer cannot be avoided; and the like {see "Purasuchikku Zairyo Koza (5), Porikaboneto Jushi (Lecture of Plastic Materials (5), Polycarbonate resins)", pages 62–67, written by Mikio Matsukane et al. and published by Nikkan Kogyo Shinbunsha (1969)}. For solving the above-mentioned problems, various attempts have been made with respect to catalysts, stabilizers, polymerization methods and the like. Especially, in the specification of WO 95/03351 (corresponding to U.S. Pat. No. 5,596,067), the present inventors have disclosed a method for producing an aromatic polycarbonate by conducting a polymerization reaction in which a molten mixture of an aromatic dihydroxy compound and a diaryl carbonate or a prepolymer obtained by the reaction of an aromatic dihydroxy compound with a diaryl carbonate is allowed to pass downwardly through a perforated plate and fall freely, so that polymerization is effected during the free-fall. By this method, a high quality aromatic polycarbonate with no discoloration can be obtained. Further, U.S. Pat. No. 5,589,564 discloses a method for producing an aromatic polycarbonate in which the above-mentioned molten mixture or prepolymer is allowed to fall along and in contact with a guide (wire) (i.e., wire-wetting fall), so that polymerization is effected during the wire-wetting fall. By this method, a high quality aromatic polycarbonate with no discoloration can be obtained. Also, a method has been proposed for producing an aromatic polycarbonate by solid phase polymerization of a diaryl carbonate with an aromatic dihydroxy compound (e.g. U.S. Pat. Nos. 4,948,871, 5,204,377 and 5,214,073), and a high quality aromatic polycarbonate can be obtained by the method.

Thus, it has become possible to obtain a high quality aromatic polycarbonate by the transesterification process. However, differing from the case of the phosgene process, in producing an aromatic polycarbonate by the transesterification process, phenol is necessarily by-produced. From the economical view-point, it is desired to utilize the by-produced phenol. Therefore, for example, in Unexamined Japanese Patent Application Laid-Open Specification Nos. 9-255772 (corresponding to U.S. Pat. No. 5,747,609) and 1060106, the by-produced phenol is recovered and utilized in the production of diphenyl carbonate (DPC). However, as described in these documents, before the by-produced phenol is utilized in the DPC production, it is necessary to subject a crude phenol product (containing the by-produced phenol) recovered from the aromatic polycarbonate production stage to purification by, for example, distillation, so as to prevent a clogging of the conduits in the DPC production stage and to improve the quality of DPC and the quality of the final aromatic polycarbonate. For example, Unexamined Japanese Patent Application Laid-Open Specification No. 10-60106 discloses that the impurities contained in the crude phenol product are as follows: a dihydroxy compound: 50 ppm or less; a transesterification catalyst (i.e., a nitrogen-containing basic compound or at least one compound selected from the group consisting of an alkali metal compound and an alkaline earth metal compound): 1 ppm or less; a mixture of phenyl salicylate, o-phenoxybenzoic acid and phenyl o-phenoxybenzoate: 50 ppm or less; and a polycarbonate oligomer: 100 ppm or less. This means not only that in the DPC production stage or in a stage before the DPC production stage, it is necessary to effect a purification of a crude phenol product by using, e.g., a phenol distillation column or a phenol rectification column, but also that complicated operations are necessarily added.

Further, a liquid withdrawn from the bottom of the above-mentioned phenol distillation column or phenol rectification column contains high concentrations of bisphenol A, diphenyl carbonate and an aromatic polycarbonate oligomer and the like separated from the crude phenol product (containing by-produced phenol). As a result, conventionally, the yield of the aromatic polycarbonate, based on either phenol or bisphenol A becomes low, and the necessity for disposal of the liquid withdrawn from the bottom of the phenol distillation column or phenol rectification column has been a problem.

As apparent from the above, a technique which makes it possible to efficiently utilize the by-produced phenol necessarily occurring during the polymerization reaction for the production of an aromatic polycarbonate by the transesterification process has not yet been established.

SUMMARY OF THE INVENTION

In this situation, for solving the above-mentioned problem accompanying the prior art, the present inventors have made extensive and intensive studies with a view toward developing a method for efficiently utilizing the phenol by-produced in the aromatic polycarbonate production. As a result, it has unexpectedly been found that the above objective can be attained by a method which comprises reacting acetone with a phenol material to produce bisphenol A, and polymerizing the bisphenol A with diphenyl carbonate to produce an aromatic polycarbonate while producing phenol as a by-product, wherein the by-product phenol is recovered as a crude phenol product containing the by-product phenol as a main component and containing impurities and the crude phenol product is used as at least a part of the phenol material for producing bisphenol A. That is, it has surprisingly been found that when the above-mentioned crude phenol product is used for the production of bisphenol A, the crude phenol product can be used without any purification or after only a rough purification. In the present invention, the crude phenol product containing, as a main component, by-product phenol (occurring during the polymerization reaction for producing an aromatic polycarbonate) and containing impurities is recycled to the bisphenol A production stage, thereby achieving advantages not only in that complicated operations, such as separation and purification of phenol from the crude phenol product and disposal of wastes, become unnecessary, but also in that the yield of the aromatic polycarbonate, based on any of phenol and bisphenol A, can be improved.

Accordingly, it is a primary object of the present invention to provide a method for producing an aromatic polycarbonate, in which a crude phenol product as such, containing, as a main component, by-product phenol (occurring in the polymerization reaction for producing an aromatic polycarbonate) and containing impurities, can be utilized for producing bisphenol A, finally for producing an aromatic polycarbonate, without any purification or the like, thereby achieving advantages not only in that a necessity for complicated operations, such as a purification treatment, can be reduced, but also in that the amount of wastes can be reduced and the yield of the aromatic polycarbonate, based on any of phenol and bisphenol A, can be improved.

The foregoing and other objects, features and advantages of the present invention will be apparent from the following detailed description and appended claims taken in connection with the accompanying drawings.

DESCRIPTION OF REFERENCE NUMERALS

Figure 1:
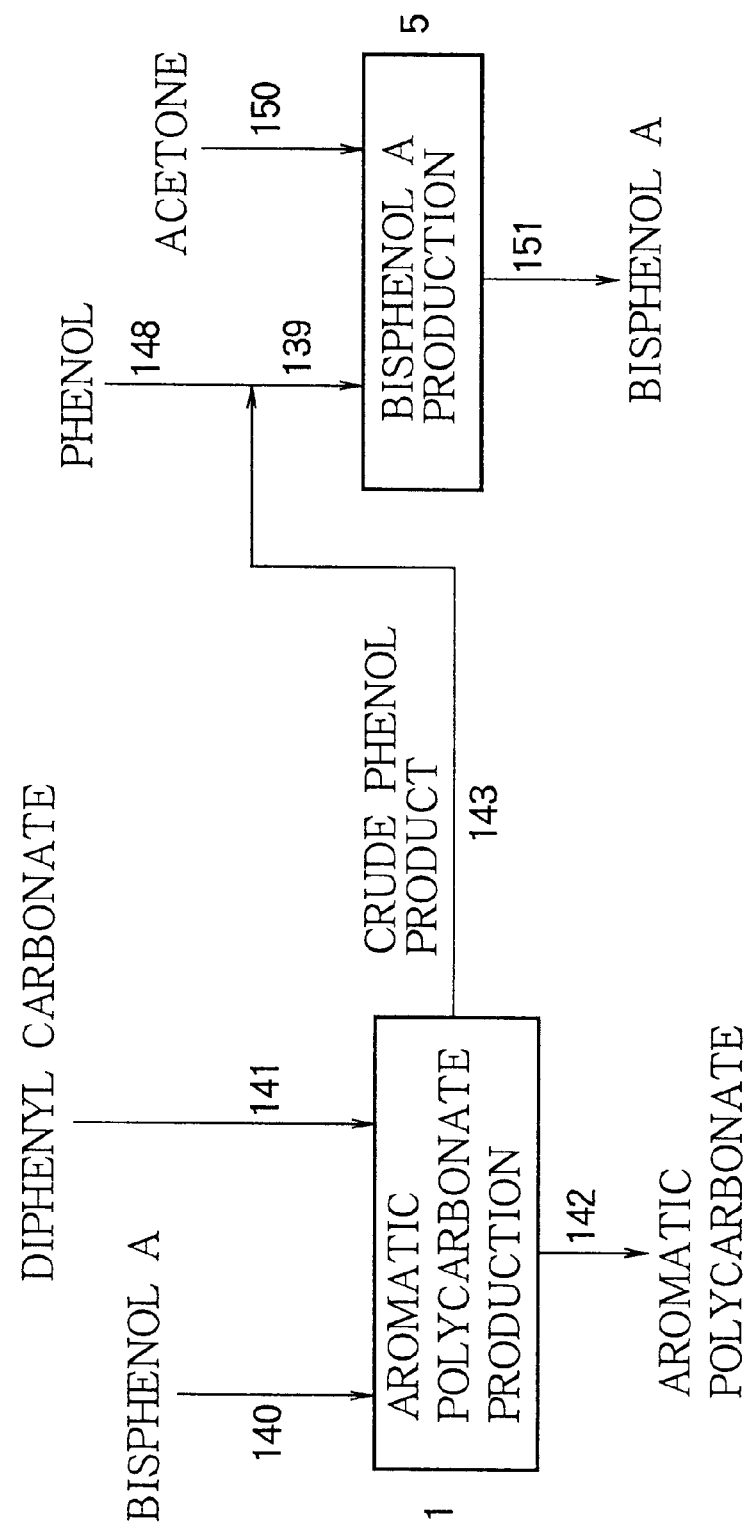
FIG. 1 is a chart showing an operation in which, according to the method of the present invention, a crude phenol product is recycled to a bisphenol A production stage.

1: aromatic polycarbonate production step
2: phenol recovering column
3: phenol purification column
4: diphenyl carbonate production step
5: bisphenol A production step
6, 8: inlet
7: bisphenol A accumulation tank
9: first stage agitation type polymerizer vessel A
10: first stage agitation type polymerizer vessel B
11: second stage agitation type polymerizer vessel
13: phenol condenser
14: roots blower
15: liquid seal-type vacuum pump
16: free-fall polymerizer
17: wire-wetting fall polymerizer
18: crude phenol product accumulation tank
19: phenol accumulation tank
20: acetone accumulation tank
21: reaction column for formation of bisphenol A
22: light low-boiling point components separation column
23: dehydration column
24: acetone recovering column
25: phenol flushing column
26: bisphenol A deposition chamber
27: centrifugal separator
28: phenol elimination column
29: steam stripping column
30: crystalline adduct melting chamber
32: dehydration column
48: perforated plate
49: molten prepolymer
50: perforated plate
51: wire-type guide
71: diphenyl carbonate accumulation tank
72: first continuous multi-stage distillation column
73: first continuous multi-stage distillation column
74: diphenyl carbonate purification column
83: first evaporator
88: evaporator 91, 86, 103, 115, 126, 133, 161: condenser
94: preheater
96, 112, 117: reboiler
102: second evaporator
128: purified phenol accumulation tank
129: phenol purification column
136: hydrolysis chamber
155: diphenyl carbonate recovering column
31, 33, 34, 35, 36, 37, 38, 40, 41, 42, 44, 45, 46, 47, 52, 53, 55, 56, 57, 58, 59, 60, 61, 62, 63, 64, 65, 66, 67, 68, 69, 70, 75, 76, 77, 78, 79, 80, 81, 82, 84, 85, 87, 89, 90, 92, 93, 95, 97, 98, 99, 100, 101, 104, 106, 107, 108, 109, 110, 111, 113, 114, 116, 118, 119, 120, 121, 122, 123, 124, 125, 127, 130, 131, 132, 134, 135, 137, 138, 139, 140, 141, 142, 143, 144, 145, 146, 147, 148, 149, 150, 151, 152, 153, 154, 156, 157, 158, 159, 160: conduit

DETAILED DESCRIPTION OF THE INVENTION

In the present invention, there is provided a method for producing an aromatic polycarbonate, which comprises:

feeding acetone and a phenol material to a reactor to effect a reaction between the acetone and the phenol material, thereby producing bisphenol A, and polymerizing the bisphenol A with diphenyl carbonate in a polymerizer to produce an aromatic polycarbonate while producing phenol as a by-product, wherein the by-product phenol is recovered from the polymerizer as a crude phenol product containing the by-product phenol as a main component and containing impurities, and the crude phenol product is used as at least a part of the phenol material for producing bisphenol A.

For an easy understanding of the present invention, the essential features and various preferred embodiments of the present invention are enumerated below.

1. A method for producing an aromatic polycarbonate, which comprises:

feeding acetone and a phenol material to a reactor to effect a reaction between the acetone and the phenol material, thereby producing bisphenol A, and polymerizing the bisphenol A with diphenyl carbonate in a polymerizer to produce an aromatic polycarbonate while producing phenol as a by-product, wherein the by-product phenol is recovered from the polymerizer as a crude phenol product containing the by-product phenol as a main component and containing impurities, and the crude phenol product is used as at least a part of the phenol material for producing bisphenol A.

2. The method according to item 1 above, wherein the crude phenol product has a purity of 50 to 99% by weight in terms of the phenol content thereof.

3. The method according to item 1 or 2 above, wherein, before the crude phenol product is used for producing bisphenol A, the crude phenol product is treated for the hydrolysis of the impurities contained therein.

4. The method according to item 1 or 2 above, wherein the bisphenol A is obtained in the molten state, and the molten state of the bisphenol A is maintained until the bisphenol A is subjected to the polymerization thereof with the diphenyl carbonate.

5. The method according to item 1 or 2 above, wherein the bisphenol A subjected to the polymerization thereof with the diphenyl carbonate is in the form of a phenol adduct thereof.

6. The method according to item 1 or 2 above, wherein the phenol material comprises phenol and at least one impurity selected from the group consisting of o-cresol, methyl o-methoxybenzoate, phenyl salicylate, o-phenoxybenzoic acid, phenyl o-phenoxybenzoate, phenyl tolyl carbonate, xanthone, a catechol derivative, diphenyl carbonate, bisphenol A and an aromatic polycarbonate oligomer.

In the method of the present invention, a crude phenol product, which is obtained in the reaction for producing an aromatic polycarbonate, can be efficiently utilized for the production of bisphenol A used as a raw material for producing an aromatic polycarbonate, without any purification or after only a rough and simple purification. Therefore, the method of the present invention is advantageous not only in that there is no need for any of a step of highly purifying the crude phenol product and a step of recovering wastes (wherein these steps are necessary when the crude phenol product is put to other uses or used for producing diphenyl carbonate), but also in that the yield of the aromatic polycarbonate, based on any of phenol and bisphenol A, is improved. Therefore, the method of the present invention can be extremely advantageously used for large-scale commercial production of an aromatic polycarbonate by the transesterification process. It is totally unexpected from the prior art that the crude phenol product, which is obtained in the production of an aromatic polycarbonate, can be used as at least a part of the phenol material for producing bisphenol A, without any purification or only after a rough purification, thereby achieving advantages not only in that complicated operations, such a high purification of the crude phenol product, become unnecessary, but also in that the yield of the aromatic polycarbonate can be improved.

Figure 2:
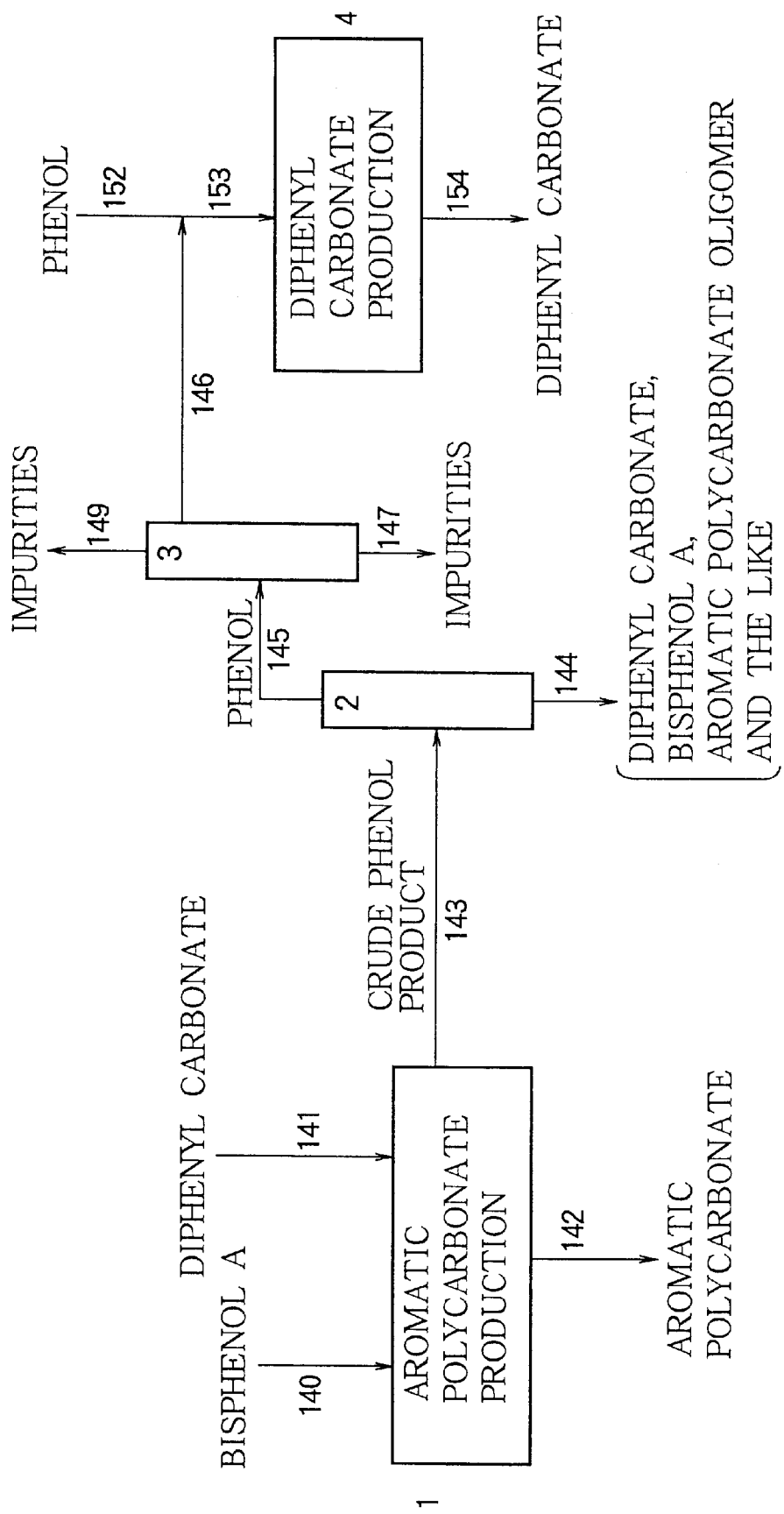
FIG. 2 is a chart showing an operation in which, according to a conventional method, a crude phenol product is recycled to a diphenyl carbonate production stage, wherein the crude phenol product is subjected to a purification treatment prior to recycling.

In order to further clarify the effects of the present invention, an explanation is made below, referring to FIG. 2, with respect to the conventionally proposed method for producing an aromatic polycarbonate, wherein the crude phenol product is purified and used in production of diphenyl carbonate (DPC).

The crude phenol product, which is recovered from stage 1 for producing an aromatic polycarbonate from bisphenol A and diphenyl carbonate, contains not only by-product phenol as a main component but also diphenyl carbonate, bisphenol A, an aromatic polycarbonate oligomer and the like. If the crude phenol product as such is fed to diphenyl carbonate production stage 4, problems arise that a clogging of the conduits occurs and the quality of DPC is lowered, and also the quality of the final aromatic polycarbonate is lowered (see Unexamined Japanese Patent Application Laid-Open Specification No. 10-60106). Therefore, the crude phenol product has to be purified. For this purpose, the crude phenol product is first fed to phenol recovering column 2 through conduit 143.

Diphenyl carbonate, bisphenol A and an aromatic polycarbonate oligomer and the like, which have been separated from the crude phenol product, are withdrawn from the bottom of phenol recovering column 2 through conduit 144. On the other hand, phenol is withdrawn from the top of phenol recovering column 2. Unexamined Japanese Patent Application Laid-Open Specification No 10-60106 has a description to the effect that, when the phenol which is withdrawn from the top of phenol recovering column 2 still contains a trace amount of impurities, such as bisphenol A, a nitrogen-containing basic compound, an alkali metal compound, an alkaline earth metal compound, boric acid or a boric acid ester, ammonium hydrogen phosphite, phenyl salicylate, o-phenoxybenzoic acid, phenyl o-phenoxybenzoate and the like, it is necessary to more highly purify the phenol before it is used in diphenyl carbonate production stage 4. Therefore, the phenol withdrawn from the top of phenol recovering column 2 is fed to phenol purification column 3 through conduit 145. The impurities separated from the phenol in phenol purification column 3 are withdrawn from the top or bottom of column 3, and a highly purified phenol is withdrawn from column 3 through conduit 146. The highly purified phenol withdrawn from column 3 is mixed with fresh phenol and the resultant mixture is fed to diphenyl carbonate production stage 4. With respect to the mixture which is withdrawn from the bottom of phenol recovering column 2 through conduit 144, if this mixture is recycled to aromatic polycarbonate production stage 1, the polymerization reaction system would become unstable. Therefore, the mixture as such cannot be recycled to aromatic polycarbonate production stage 1, and the mixture has to be disposed of as wastes, or utilized as a fuel to achieve a recovery of heat, or subjected to thinfilm distillation or the like in order to recover diphenyl carbonate. When this mixture is subjected to thin-film distillation by means of a thin-film distillation column (not shown), a polymerization reaction is likely to occur at the bottom of the thin-film distillation column, so that a clogging of conduits is likely to occur. Further, the impurities withdrawn from phenol purification column 3 through conduits 147 and 149 have to be disposed of as wastes or utilized as a fuel.

As is apparent from the above, in the conventional technique, wherein the crude phenol product is used as a material for producing diphenyl carbonate, complicated operations, waste disposal and a loss of the raw materials cannot be avoided.

On the other hand, in the method of the present invention, as shown in FIG. 1, the crude phenol product (recovered from aromatic polycarbonate production stage 1) as such, containing the by-product phenol as a main component and containing impurities, can be fed to bisphenol A production stage 5, so that complicated operations and waste disposal are not necessary. Therefore, the method of the present invention is advantageous in that not only do the involved operations become very simple, but also the yield of the aromatic polycarbonate, based on any of phenol and bisphenol A, can be improved.

Hereinbelow, the present invention will be described in more detail.

First, an explanation will be made with respect to aromatic polycarbonate production stage 1 in the method of the present invention, wherein an aromatic polycarbonate is produced by a transesterification between diphenyl carbonate and bisphenol A.

There is no particular limitation with respect to the polymerization method for producing an aromatic polycarbonate as long as the transesterification process is employed. Any of known polymerizers for use in producing an aromatic polycarbonate by the transesterification process can be used in the method of the present invention. Examples of various known reaction modes usable in the method of the present invention include a reaction mode in which an agitation type polymerizer (having a vertically or horizontally extending agitator), a thin-film evaporation type polymerizer, a screw type polymerizer or the like is used, a reaction mode in which a polymerizable material is allowed to pass downwardly through a perforated plate and fall freely to thereby effect a polymerization during the free-fall, a reaction mode in which a polymerizable material is allowed to pass downwardly through a perforated plate having a guide extending downwardly therefrom and fall along and in contact with the guide to thereby effect a polymerization during the fall along and in contact with the guide, and a reaction mode in which a solid state polymerization is effected. For producing a high quality aromatic polycarbonate, especially preferred are a reaction mode in which a polymerizable material is allowed to pass downwardly through a perforated plate and fall freely to thereby effect a polymerization during the free-fall (see U.S. Pat. No. 5,596,067), a reaction mode in which a polymerizable material is allowed to pass downwardly through a perforated plate having a guide (wire) extending downwardly therefrom and fall along and in contact with the guide (i.e., wire-wetting fall) to thereby effect a polymerization during the wire-wetting fall (see U.S. Pat. No. 5,589,564), and a reaction mode in which a solid state polymerization is effected (see in U.S. Pat. No. 4,948,871, U.S. Pat. No. 5,204,377 and U.S. Pat. No. 5,214,073). It is also preferred that these reaction modes are employed in combination.

The ratio in which bisphenol A and diphenyl carbonate are used (i.e., a charging ratio) may vary depending on the polymerization temperature and other polymerization conditions. Diphenyl carbonate is generally used in an amount of from 0.9 to 2.5 moles, preferably from 0.95 to 2.0 moles, more preferably from 0.98 to 1.5 moles, per mole of bisphenol A.

The number average molecular weight of the aromatic polycarbonate obtained according to the method of the present invention is generally from 500 to 100,000, preferably from 2,000 to 30,000.

In the present invention, the reaction temperature for reacting bisphenol A with diphenyl carbonate for producing an aromatic polycarbonate is generally in the range of from 50 to 350° C., preferably from 100 to 290° C.

As the reaction proceeds, phenol is by-produced. By removing phenol from the reaction system, the reaction rate can be increased. Therefore, in the method of the present invention, it is preferred to employ a method in which an inert gas which does not adversely affect the reaction, such as nitrogen, argon, helium, carbon dioxide and a lower hydrocarbon gas, is introduced so that the by-produced phenol is entrained by the inert gas, and the inert gas entraining the phenol is withdrawn to remove the by-produced phenol, or a method in which the reaction is carried out under reduced pressure. The preferred reaction pressure may vary depending on the molecular weight of the aromatic polycarbonate to be produced, the polymerization temperature and the like. For example, when the number average molecular weight of the aromatic polycarbonate is less than 1,000, the reaction pressure is preferably from higher than 6,665 Pa (50 mmHg) to atmospheric pressure. When the number average molecular weight is from 1,000 to 2,000, the reaction pressure is preferably from 400 Pa (3 mmHg) to 6,665 Pa (50 mmHg). When the number average molecular weight is greater than 2,000, the reaction pressure is preferably 2,666 Pa (20 mmHg) or less, more preferably 1,333 Pa (10 mmHg) or less, most preferably 267 Pa (2 mmHg) or less. It is preferred that the reaction is performed under reduced pressure while introducing the above-mentioned inert gas.

When the by-product phenol is removed from the reaction system, the by-product phenol is accompanied with diphenyl carbonate, bisphenol A, an aromatic polycarbonate oligomer and the like. As a result, the by-product phenol is removed from the reaction system in the form of a low purity phenol. It is possible to separate and remove, to some extent, diphenyl carbonate, bisphenol A, an aromatic polycarbonate oligomer and the like from this low purity phenol by subjecting this low purity phenol to partial condensation or distillation. However, diphenyl carbonate, bisphenol A, an aromatic polycarbonate oligomer and the like cannot be completely removed by these procedures. In the present invention, the term "crude phenol product" means an impurity-containing phenol which is obtained by a method in which phenol by-produced in the polymerization reaction system for producing an aromatic polycarbonate is removed and recovered from the reaction system, wherein the impurity-containing phenol contains the by-product phenol as a main component and contains at least one impurity selected from the group consisting of by-products other than the by-product phenol, remaining unreacted raw materials for the polymerization (i.e., diphenyl carbonate and bisphenol A) and an aromatic polycarbonate oligomer.

Examples of by-products other than the by-product phenol include o-cresol, methyl o-methoxybenzoate, phenyl salicylate, o-phenoxybenzoic acid, phenyl o-phenoxybenzoate, phenyl tolyl carbonate, xanthone, a catechol derivative and the like.

Further examples of crude phenol products include phenol obtained by subjecting an impurity-containing phenol (obtained by a method in which phenol by-produced in the polymerization reaction system for producing an aromatic polycarbonate is removed and recovered from the reaction system) to partial condensation or distillation so as to separate diphenyl carbonate, bisphenol A, a polycarbonate oligomer and the like, as long as the phenol contains at least one impurity selected from the group consisting of by-products other than the by-product phenol, remaining unreacted raw materials for the polymerization and an aromatic polycarbonate oligomer. In the present invention, the crude phenol product is used as at least a part of the phenol material for producing bisphenol A. There is no particular limitation with respect to the proportion of the crude phenol product in the phenol material. It is preferred that the proportion of the crude phenol product in the phenol material is in the range of from 10 to 100% by weight, more advantageously from 50 to 100% by weight, still more advantageously from 70 to 100% by weight, based on the weight of the phenol material.

A transesterification reaction can be carried out in the absence of a catalyst. However, if it is desired to promote the polymerization, the polymerization can be effected in the presence of a catalyst. The polymerization catalysts which are customarily used in the art can be used without particular limitation. Examples of such catalysts include hydroxides of an alkali metal and of an alkaline earth metal, such as lithium hydroxide, sodium hydroxide, potassium hydroxide and calcium hydroxide; alkali metal salts of, alkaline earth metal salts of and quaternary ammonium salts of boron hydride and of aluminum hydride, such as lithium aluminum hydride, sodium boron hydride and tetramethyl ammonium boron hydride; hydrides of an alkali metal and of an alkaline earth metal, such as lithium hydride, sodium hydride and calcium hydride; alkoxides of an alkali metal and of an alkaline earth metal, such as lithium methoxide, sodium ethoxide and calcium methoxide; aryloxides of an alkali metal and of an alkaline earth metal, such as lithium phenoxide, sodium phenoxide, magnesium phenoxide, LiO-Ar-OLi wherein Ar represents an aryl group, and NaO-Ar-ONa wherein Ar is as defined above; organic acid salts of an alkali metal and of an alkaline earth metal, such as lithium acetate, calcium acetate and sodium benzoate; zinc compounds, such as zinc oxide, zinc acetate and zinc phenoxide; boron compounds, such as boron oxide, boric acid, sodium borate, trimethyl borate, tributyl borate, triphenyl borate, ammonium borates represented by the formula: $(R^3 R^4 R^5 R^6) NB(R^3 R^4 R^5 R^6)$, and phosphonium borates represented by the formula: $(R^3 R^4 R^5 R^6)PB(R^3 R^4 R^5 R^6)$, wherein each of $R^3$, $R^4$, $R^5$ and $R^6$ independently represents a group selected from the group consisting of a $C_1$–$C_{10}$ alkyl group, a $C_1$–$C_{10}$ alkoxy group, a $C_5$–$C_{10}$ cycloalkyl group, a $C_6$–$C_{10}$ carbocyclic aromatic group and a $C_6$–$C_{10}$ carbocyclic aralkyl group (one or more hydrogen atoms in $R^3$, $R^4$, $R^5$ and $R^6$ may be substituted with other substituent group, such as a halogen atom, a $C_1$–$C_{10}$ alkyl group, a $C_1$–$C_{10}$ alkoxy group, a phenyl group, a phenoxy group, a vinyl group, a cyano group, an ester group, an amide group, a nitro group and the like, as long as the substituent group does not adversely affect the reaction); silicon compounds, such as silicon oxide, sodium silicate, tetraalkylsilicon, tetraarylsilicon and diphenyl-ethyl-ethoxysilicon; germanium compounds, such as germanium oxide, germanium tetrachloride, germanium ethoxide and germanium phenoxide; tin compounds, such as tin oxide, dialkyltin oxide, dialkyltin carboxylate, tin acetate, tin compounds having an alkoxy group or aryloxy group bonded to tin, such as ethyltin tributoxide, and organotin compounds; lead compounds, such as lead oxide, lead acetate, lead carbonate, basic lead carbonate, and alkoxides and aryloxides of lead or organolead; onium compounds, such as a quaternary ammonium salt, a quaternary phosphonium salt and a quaternary arsonium salt; antimony compounds, such as antimony oxide and antimony acetate; manganese compounds, such as manganese acetate, manganese carbonate and manganese borate; titanium compounds, such as titanium oxide and titanium alkoxides and titanium aryloxide; and zirconium compounds, such as zirconium acetate, zirconium oxide, zirconium alkoxide, zirconium aryloxide and zirconium acetylacetone.

These catalysts can be used individually or in combination. The amount of the catalysts to be used is generally in the range of from $10^{-8}$ to 1% by weight, preferably from $10^{-7}$ to $10^{-1}$% by weight, based on the weight of bisphenol A.

With respect to materials for constructing the reactors and polymerizers used in the method of the present invention, there is no particular limitation. However, stainless steel, nickel or glass is generally used as a material for at least inner wall portions of polymerizers.

Next, an explanation will be made with respect to the bisphenol A production, wherein the crude phenol product recovered from the aromatic polycarbonate production stage is used as at least a part of the phenol material. When the crude phenol product is used as only a part of the phenol material, fresh phenol can be used as the remainder of the phenol material. In the present invention, there is no particular limitation with respect to the method for producing bisphenol A, as long as the method comprises reacting acetone with the phenol material in the presence of an acid catalyst to thereby produce bisphenol A. Usually, a method using anhydrous hydrogen chloride as a catalyst or a method using a cation exchange resin as a catalyst is employed {with respect to the former, reference can be made to G. E. Haddeland & T. H. Vandenbosh: *Bisphenol-A & Phosgene, Process Economics Program*, Stanford Research Institute, M. P. California, Report No. 81 (November 1972) and the like; and, with respect to the latter, reference can be made to *UCC, Dow, Shell BPA Process*, Fairfield Associates Inc., Westport, Conn., Fairfield Report (September 1980)}.

The bisphenol A production method using anhydrous hydrochloride as a catalyst comprises a reaction step, a separation-recovery step and a distillation-purification step. In the reaction step, phenol and acetone are subjected to a condensation reaction under conditions wherein the temperature is approximately 50° C., the pressure is atmospheric pressure or a slightly superatmospheric pressure, and the molar ratio of phenol to acetone is approximately 4:1, to thereby produce bisphenol A, while by-producing water. In the separation-recovery step, hydrogen chloride dissolved in the by-produced water (i.e., hydrochloric acid) is recovered, and phenol and isomers thereof are separated and recovered, whereby a crude bisphenol A is obtained. The recovered hydrochloric acid, phenol and isomers are recycled to the reaction step. In the distillationpurification step, the crude bisphenol A is subjected to distillation, crystallization, separation, washing and drying, to thereby obtain a highly purified bisphenol A.

The bisphenol A production method using a cation exchange resin as a catalyst comprises a reaction step, a separation-recovery step, a purification step and a thermal cracking-isomerization step. In the reaction step, phenol and acetone are subjected a condensation reaction under conditions wherein the temperature is approximately 50 to 90° C., the pressure is atmospheric pressure, and the molar ratio of phenol to acetone is approximately 10:1, thereby producing bisphenol A, while by-producing water. In the separation-recovery step, the by-produced water is separated, and acetone and phenol are separated and recovered. The recovered acetone and phenol are recycled to the reaction step. In the purification step, a crystallization of bisphenol A is conducted so that crystals of bisphenol A are deposited in the form of a phenol adduct, and the obtained crystals are washed, subjected to distillation for separating phenol, and then granulated, to thereby obtain a purified bisphenol A. The separated phenol is utilized for producing bisphenol A. Isomers and tarry components separated from bisphenol A by the crystallization of bisphenol A are fed to the thermal crackingisomerization step, wherein they are converted to phenol, bisphenol A and isomers of bisphenol A and then recycled to the reaction step.

In the present invention, the crude phenol product recovered from the polymerizer used for producing an aromatic polycarbonate is used as at least a part of the phenol material for producing bisphenol A. As mentioned above, the purity of the crude phenol product varies depending on the temperature, the degree of vacuum and the polymerization apparatus employed in the polymerization step, and also varies depending on the degree of recycling, to the aromatic polycarbonate polymerizer, of diphenyl carbonate, bisphenol A, an aromatic polycarbonate oligomer and the like which are separated by partial condensation or rough distillation performed on the crude phenol product to an extent such as not to cause a loss. However, in general, the crude phenol product contains 1–50% by weight of unreacted diphenyl carbonate, unreacted bisphenol A, an aromatic polycarbonate oligomer and the like. That is, the crude phenol product has a purity of 50 to 99% by weight in terms of the phenol content thereof. As mentioned above, when the by-product phenol is recycled to the diphenyl carbonate production stage according to the conventional technique, the crude phenol product is required to be highly purified. However, in the present invention, even if the crude phenol product contains impurities, such as bisphenol A and the like, no problem occurs. It would be rather preferred that, in order to avoid not only a necessity for complicated operations required for highly purifying the crude phenol product but also a lowering of the yield of the aromatic polycarbonate, based on either phenol or bisphenol A, due to a loss caused by the purification, the crude phenol product is recycled to the reactor for producing bisphenol A without any purification or after only rough purification. It is preferred that the purity of the crude phenol product is in the range of 70 to 99% by weight in terms of the phenol content thereof, more advantageously 80 to 99% by weight, especially advantageously 90 to 99% by weight. When the purity of the crude phenol product is less than 50% by weight, not only the production efficiency in the bisphenol A production stage but also the stability of the reaction system for producing bisphenol A tends to be lowered.

The reaction system for producing bisphenol A usually contains water (by-produced during the reaction) and an acid catalyst and has a temperature of 50 to 90° C. Under these conditions, diphenyl carbonate contained in the crude phenol product which is fed to the reaction system for producing bisphenol A is hydrolyzed to phenol. On the other hand, bisphenol A in the crude phenol product, as such, is transferred to a subsequent separation-recovery step, whereas the aromatic polycarbonate oligomer in the crude phenol product is hydrolyzed to bisphenol A and transferred to a subsequent separation-recovery step. As mentioned above, the diphenyl carbonate and the aromatic polycarbonate oligomer contained in the crude phenol product are hydrolyzed in the reaction step for producing bisphenol A. However, even if the diphenyl carbonate and/or the aromatic polycarbonate oligomer remains unreacted in the reaction step for producing bisphenol A and is transferred to a subsequent separation-recovery step, the diphenyl carbonate and/or the aromatic polycarbonate oligomer is separated and recovered in the subsequent separation-recovery step, and recycled, as such, to the above-mentioned reaction step for producing bisphenol A or subjected to hydrolysis treatment and converted to phenol and/or bisphenol A, which is then recycled to the above-mentioned reaction step for producing bisphenol A. Therefore, no problem occurs. Further, when a large amount of diphenyl carbonate remains unreacted, it is possible that the diphenyl carbonate forms an adduct with phenol, and the diphenyl carbonate in the form of the adduct remains in the purified bisphenol A. However, diphenyl carbonate is a monomer used in the aromatic polycarbonate production stage. Therefore, the diphenyl carbonate remaining in the purified bisphenol A does not adversely affect the quality of the aromatic polycarbonate as a final product.

As mentioned above, the impurities (diphenyl carbonate and/or aromatic polycarbonate oligomer) contained in the crude phenol product are hydrolyzed in the reaction system for producing bisphenol A. However, when it is intended to more surely hydrolyze the impurities, the impurities contained in the crude phenol product can be hydrolyzed before the crude phenol product is used for producing bisphenol A. As examples of methods for conducting a hydrolysis of the impurities contained in the crude phenol product before the crude phenol product is used for producing bisphenol A, there can be mentioned a method comprising adding water to the crude phenol product and heating the resultant mixture at a temperature of 50 to 200° C., and a method comprising combining the crude phenol product with a water-containing unreacted acetone which is recovered in the separation step in the production of bisphenol A (and is usually adapted to be fed to the reaction step for producing bisphenol A) and heating the resultant mixture at 50 to 150° C. It is preferred that the amount of water for performing the above-mentioned hydrolysis in the hydrolysis reaction system is at least equimolar to the total molar amount of the components to be hydrolyzed (such as diphenyl carbonate and an aromatic polycarbonate oligomer contained in the crude phenol product). Generally, the upper limit of the molar amount of water is preferably 10 times as large as the molar amount of the components to be hydrolyzed.

Further, it is preferred that the reaction is performed for a time sufficient to perform a desired hydrolysis, generally from 1 minute to 3 hours.

Further, in the method of the present invention, the apparatus for the production of bisphenol A and the apparatus for the production of an aromatic polycarbonate need not be physically connected to each other, as long as the crude phenol product recovered from the polymerizer used for the polymerization reaction for producing an aromatic polycarbonate can be used as at least a part of the phenol material for producing bisphenol A. However, in the present invention, it is preferred that the crude phenol product recovered from the aromatic polycarbonate production stage is recycled to the apparatus for producing bisphenol A, wherein the apparatus for producing an aromatic polycarbonate is physically connected to the apparatus for producing bisphenol A through conduits or the like. Further, prills obtained by prilling bisphenol A obtained in a molten state in the bisphenol A production stage may be fed to the aromatic polycarbonate production stage. However, it is also preferred to feed bisphenol A in a molten state as such (i.e., without prilling) through conduits to the aromatic polycarbonate production stage while maintaining the molten state of bisphenol A until the bisphenol A is subjected to polymerization with diphenyl carbonate. Bisphenol A is usually obtained in the form of a phenol adduct. It is also preferred that bisphenol A in the form of a phenol adduct as such is fed to the aromatic polycarbonate production stage and polymerized with diphenyl carbonate. As mentioned above, bisphenol A in the molten state may be fed to the aromatic polycarbonate production stage without prilling. This is advantageous in that the prilling operation and the subsequent handling of the prills can be omitted.

As mentioned above, it is preferred to feed bisphenol A in the form of a phenol adduct as such to the aromatic polycarbonate production stage; this is advantageous in that the purification step and prilling step of bisphenol A can be omitted. However, in this case, it is noted that the amount of phenol recovered and recycled from the polymerization reaction system for the production of an aromatic polycarbonate is increased.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, various properties were measured as follows.
(1) Measurement of the purity of phenol:
 The purity of phenol was measured by high performance liquid chromatography (HPLC) (SCL-6B, manufactured and sold by Shimadzu Corporation, Japan).
(2) Measurement of the weight average molecular weight of a polycarbonate:
 The weight average molecular weight of an aromatic polycarbonate was measured by gel permeation chromatography (GPC) (column: TSK-GEL, manufactured and sold by Tosoh Corp., Japan; and solvent: THF).
(3) Evaluation of the color of an aromatic polycarbonate:
 An aromatic polycarbonate was subjected to molding, by means of an injection molding machine (J100E, manufactured and sold by THE JAPAN STEEL WORKS. LTD., Japan), at a cylinder temperature of 290° C. and a mold temperature of 90° C. to obtain a test specimen having a 50 mm length, a 50 mm width and a 3.2 mm thickness. The color of the aromatic polycarbonate was evaluated, using the specimen, in accordance with the CIELAB method (Comission Internationale de l'Eclairage 1976 L*a*b* Diagram), and the yellowness of the specimen is expressed in terms of the b*-value. The larger the b*-value of the specimen, the higher the yellowness of the specimen.
(4) Evaluation of the APHA (American Public Health Association) value of the color of bisphenol A in a molten state:
 1.245 g of potassium chloroplatinate and 1.000 g of cobalt chloride were dissolved in 100 ml of concentrated hydrochloric acid to thereby obtain a solution, and distilled water was added to the obtained solution so that the volume of the solution became 1,000 ml, thereby obtaining a mother standard solution having an APHA value of 500. Further, the obtained mother standard solution was diluted, so that ten different types of stepwise diluted standard solutions were prepared, wherein the stepwise diluted standard solutions have different degrees of dilution so as to have APHA values of 1 to 10.

30 g of bisphenol A was melted by heating at 175° C. for 1 hour in a heat-resistant test tube, and the APHA value of the color of the resultant molten bisphenol A was evaluated by visual comparison of the color of the molten bisphenol A with the colors of the above-mentioned stepwise diluted standard solutions.

For obtaining an aromatic polycarbonate having a low b*-value (i.e., a low yellowness), it is preferred that the APHA value of bisphenol A used for the production of an aromatic polycarbonate is 10 or less.

Example 1

Figure 3:
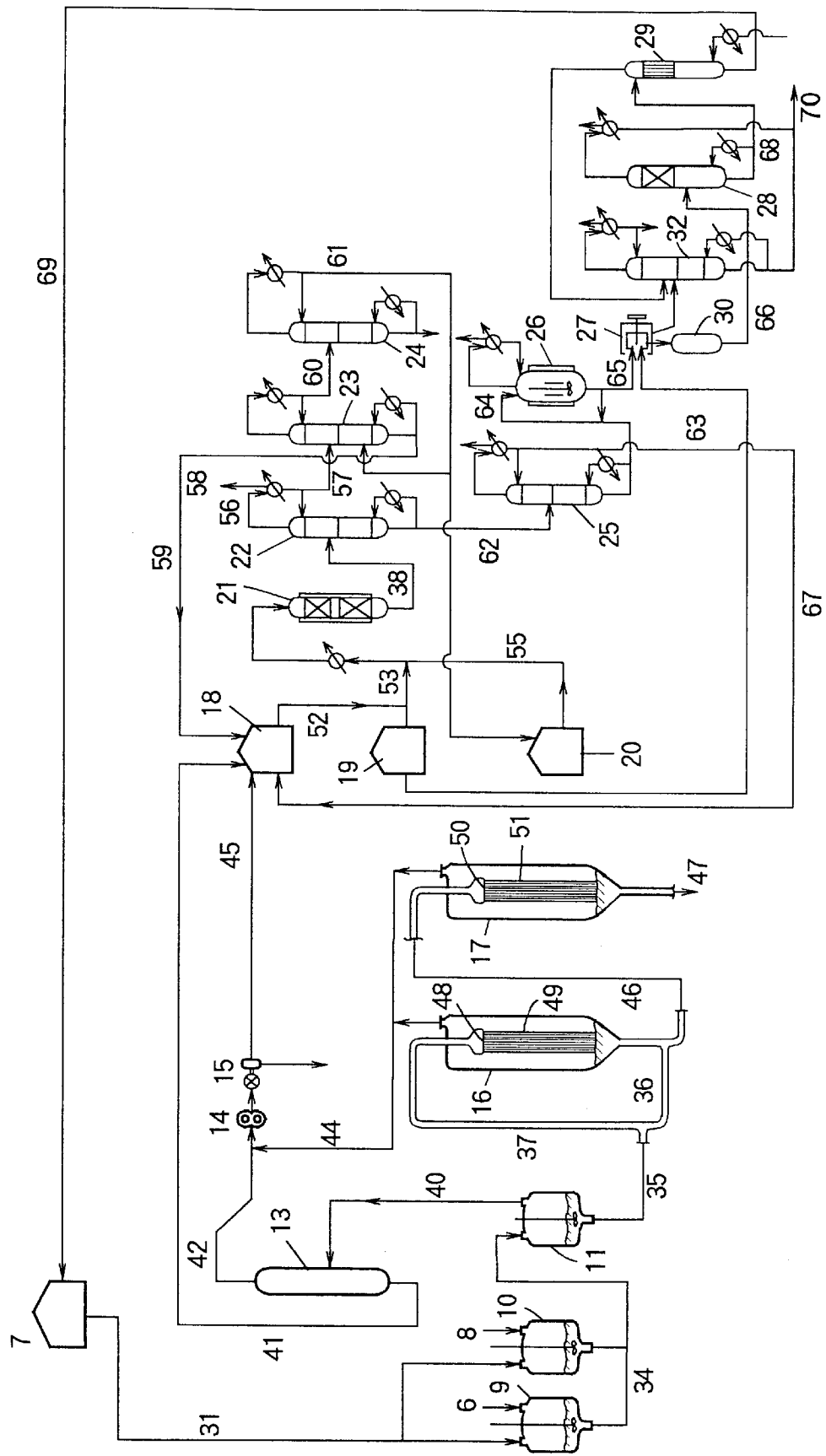
FIG. 3 is a diagram showing the system used in Example 1 for producing an aromatic polycarbonate.

An aromatic polycarbonate was produced in accordance with a system as shown in FIG. 3. The system of FIG. 3 comprises (i) a bisphenol A production stage comprising a step for effecting a reaction of acetone with a phenol material (conducted using reaction column 21 for formation of bisphenol A) and a step for purifying bisphenol A (conducted using a bisphenol A purification system comprising light low-boiling point components separating column 22, phenol flushing column 25, bisphenol A deposition chamber 26, centrifugal separator 27, phenol elimination column 28 and steam stripping column 29); and (ii) an aromatic polycarbonate production stage wherein a crude phenol product is produced as a by-product and recycled to the above-mentioned reaction column 21 for formation of bisphenol A. The above-mentioned aromatic polycarbonate production stage comprises a first stage and a second stage agitation polymerization (conducted using first stage agitation type polymerizer vessels 9 and 10 and second stage agitation type polymerizer vessel 11, respectively), a freefall polymerization (conducted using freefall polymerizer 16), and a wire-wetting fall polymerization (conducted using wire-wetting fall polymerizer 17).
<Aromatic polycarbonate production>
 The first stage agitation type polymerization was batchwise conducted in first stage agitation type polymerizer vessels 9 and 10. The polymerization reaction conditions in both of first stage agitation type polymerizer vessels 9 and 10 were as follows: the reaction temperature was 180° C., the reaction pressure was atmospheric pressure, and the flow rate of nitrogen gas was 1 liter/hr.

Prior to the operation, bisphenol A produced and purified in the stage for producing bisphenol A was collected in bisphenol A accumulation tank 7. In operation, 40 kg of bisphenol A in bisphenol A accumulation tank 7 was batchwise charged into first stage agitation type polymerizer vessel 9 through conduit 31. Then, 40 kg of diphenyl carbonate was batchwise charged into first stage agitation type polymerizer vessel 9 through inlet 6. The resultant monomer mixture in polymerizer 9 was polymerized in a molten state while agitating for 4 hours to obtain a molten prepolymer (a). The obtained molten prepolymer (a) was continuously fed to second stage agitation type polymerizer vessel 11 at a flow rate of 7.8 kg/hr through conduit 34. While feeding molten prepolymer (a) obtained in first stage agitation type polymerizer vessel 9 to second stage agitation type polymerizer vessel 11, 40 kg of bisphenol A in bisphenol A accumulation tank 7 was batchwise charged into first stage agitation type polymerizer vessel 10 through conduit 31 and then, 40 kg of diphenyl carbonate was batchwise charged into first stage agitation type polymerizer vessel 10 through inlet 8, whereupon first stage agitation type polymerizer vessel 10 was operated to polymerize the resultant monomer mixture in the same manner as in the agitation polymerization in first stage agitation type polymerizer vessel 9, to thereby obtain a molten prepolymer (b). When first stage agitation type polymerizer vessel 9 became empty, the feeding of molten prepolymer (b) from first stage agitation type polymerizer vessel 10 to second stage agitation type polymerizer vessel 11 was started, and molten prepolymer (b) was continuously fed to second stage agitation type polymerizer vessel 11 at a flow rate of 7.8 kg/hr. With respect to the batchwise polymerization in first stage agitation type polymerizer vessels 9 and 10 and to the alternate feedings of molten prepolymers (a) and (b) from polymerizers 9 and 10, the same operations as mentioned above were repeated, so that the prepolymer {either molten prepolymer (a) or molten prepolymer (b), alternately} was continuously fed to second stage agitation type polymerizer vessel 11.

In second stage agitation type polymerizer vessel 11, a further agitation polymerization of molten prepolymers (a) and (b), alternately fed from first stage agitation type polymerizer vessels 9 and 10, was continuously carried out under polymerization reaction conditions wherein the reaction temperature was 240° C., and the reaction pressure was 70 mmHg, thereby obtaining prepolymer (c).

When the volume of prepolymer (c) in second stage agitation type polymerizer vessel 11 reached 20 liters, a portion of prepolymer (c) was continuously fed to free-fall polymerizer 16 through conduits 35 and 37 at a rate such that the volume of prepolymer (c) in second stage agitation type polymerizer vessel 11 was constantly maintained at 20 liters.

In order to reduce the load of the vacuum pump, a crude phenol product (containing bisphenol A, diphenyl carbonate and the like) distilled from second stage agitation type polymerizer vessel 11 was fed to phenol condenser 13 set at 60° C. through conduit 40. The crude phenol product obtained from the bottom of phenol condenser 13 was led into accumulation tank 18 for crude phenol product through conduit 41. An evaporated gas distilled from the top of phenol condenser 13 was led into roots blower 14 through conduit 42 and was led into liquid seal-type vacuum pump 15, in which a sealing liquid is comprised mainly of phenol. Phenol contained in the above-mentioned evaporated gas was led into accumulation tank 18 for crude phenol product through conduit 45, together with the sealing liquid.

In free-fall polymerization of prepolymer (c), free-fall polymerizer 16 was used. Free-fall polymerizer 16 has a perforated plate 48 which has 80 holes having a diameter of 5 mm. The free-fall distance is 8 m. In free-fall polymerizer 16, prepolymer (c) fed to the feeding zone (having perforated plate 48) from conduit 37 was allowed to pass through perforated plate 48 and fall freely in the form of filaments 49 to perform a free-fall polymerization under conditions wherein the reaction temperature was 250° C. and the reaction pressure was 5 mmHg, thereby obtaining prepolymer (d), while recycling a portion of prepolymer (d) to the feeding zone of polymerizer 16 through conduits 36 and 37 at a flow rate of 50 kg/hr. A crude phenol product (containing bisphenol A, diphenyl carbonate and the like) distilled from the top of free-fall polymerizer 16 was led into liquid-seal type vacuum pump 15 through conduits 44 and 42, and roots blower 14, and led into crude phenol product accumulation tank 18 through conduit 45. When the volume of prepolymer at the bottom of free-fall polymerizer 16 reached a predetermined level, a portion of prepolymer (d) was continuously fed to wire-wetting fall polymerizer 17 at a rate such that the volume of prepolymer (d) in free-fall polymerizer (d) was constantly maintained at the predetermined level.

Wire-wetting fall polymerizer 17 has a perforated plate 50 which has 80 holes having a diameter of 5 mm. In wire-wetting fall polymerizer 17, 80 strands of 1 mm φ SUS 316 L wires 51 are hung vertically from the respective holes of perforated plate 50 to the reservoir portion at the bottom of wire-wetting fall polymerizer 17 so that a polymerizing material will not fall freely (i.e., free-fall) but fall along and in contact with the wires 51 (i.e., wire-wetting fall). The wire-wetting fall distance is 8 m.

In wire-wetting fall polymerizer 17, a wire-wetting fall polymerization was continuously carried out under polymerization reaction conditions wherein the reaction temperature was 265° C. and the reaction pressure was 0.3 mmHg, while withdrawing the produced aromatic polycarbonate from the bottom of wire-wetting fall polymerizer 17 at a flow rate of about 4.4 kg/hr. A crude phenol product (containing bisphenol A, diphenyl carbonate and the like) distilled from the top of wire-wetting fall polymerizer 17 was led into liquid seal-type vacuum pump 15 through conduits 44, 42 and roots blower 14. A sealing liquid in liquid seal-type vacuum pump 15 was withdrawn through conduit 45 so as to constantly maintain the amount of the liquid in pump 15 at a predetermined level, and the withdrawn liquid was fed into accumulation tank 18 for crude phenol product. The purity of phenol in accumulation tank 18 for crude phenol product was 90% by weight.

<Bisphenol A production>

A phenol material was withdrawn from crude phenol product accumulation tank 18 and phenol accumulation tank 19 at a flow rate of 26.3 kg/hr through conduits 52 and 53, mixed with acetone withdrawn from acetone accumulation tank 20 through conduit 55, heated to 60° C. and fed to bisphenol A production reaction column 21 through conduit 54. The weight ratio of crude phenol product to fresh phenol (crude phenol product/fresh phenol) in the phenol material was 95/5. Bisphenol A production reaction column 21 was packed with an ion exchange resin having sulfonic acid groups, and the temperature in bisphenol A production reaction column 21 was kept at 60° C. using a jacket, so that a bisphenol A production reaction was effected at 60° C. The reaction mixture obtained by the bisphenol A production reaction, which contains 16% by weight of bisphenol A, 78% by weight of phenol and 1% by weight of water, based on the weight of the reaction mixture, was withdrawn from the bottom of bisphenol A production reaction column 21 and fed to light low-boiling point components separating column 22 through conduit 38. Diphenyl carbonate was not detected in the reaction mixture.

Acetone, water, phenol and carbon dioxide were withdrawn from the top of light low-boiling point components separating column 22. Carbon dioxide was discharged by means of a vacuum pump connected to conduit 58. Phenol and acetone were, respectively, purified by means of dehydration column 23 and acetone recovering column 24, and recovered.

A solution comprising phenol and bisphenol A was withdrawn from the bottom of light low-boiling point components separating column 22, and fed to phenol flushing column 25. Phenol withdrawn from the top of phenol flushing column 25 was recovered and led to crude phenol product accumulation tank 18 through conduit 63. A mixture comprising 22% by weight of bisphenol A and 74% by weight of phenol, based on the weight of the mixture, which was withdrawn from the bottom of phenol flushing column 25, was fed to bisphenol A deposition chamber 26 through conduit 64. The mixture was kept at 50° C. in bisphenol A deposition chamber 26 at a residence time of 2 hours so as to deposit crystals of bisphenol A in the form of a phenol adduct thereof (hereinbelow, these crystals are frequently referred to as "crystalline adduct"). A mixture containing the crystalline adduct was withdrawn from the lower part of bisphenol A deposition chamber 26 and fed to centrifugal separator 27, so that the mixture was separated to phenol and crystalline adduct. The crystalline adduct was fed to crystalline adduct melting chamber 30 wherein the internal temperature thereof was kept at 150° C. and melted. The resultant molten crystalline adduct was fed to phenol elimination column 28 through conduit 66, wherein the internal temperature and internal pressure of phenol elimination column 28 were kept at 160° C. and 50 torr, respectively. Phenol was recovered from the top of phenol elimination column 28. On the other hand, bisphenol A containing 3.8% by weight of phenol was withdrawn from the bottom of phenol elimination column 28 and fed to steam stripping column 29 through conduit 68, wherein the internal temperature and pressure in steam stripping column 29 were kept at 180° C. and 10 torr, respectively. Highly purified bisphenol A was withdrawn from the bottom of steam stripping column 29 and led to bisphenol A accumulation tank 7 through conduit 69 so as to be used for the production of an aromatic polycarbonate.

The above operation using the system of FIG. 3 was continuously carried out for 800 hours to obtain an aromatic polycarbonate. Bisphenol A obtained 800 hours after the start of the operation contained phenol and a chroman compound, but the contents thereof were as low as 35 ppm and 100 ppm, respectively. Further, the APHA value of bisphenol A obtained 800 hours after the start of the operation was as low as 7.0.

As apparent from the above, the use of the crude phenol product has no harmful effects. Further, no waste occurred in the recovery of the crude phenol product from the polymerization system for producing the aromatic polycarbonate.

The obtained aromatic polycarbonate had a weight average molecular weight of 28,000. Further, it was found that the b*-value of the aromatic polycarbonate was 3.5, showing that the quality of the obtained aromatic polycarbonate was very high.

Comparative Example 1

Figure 4:
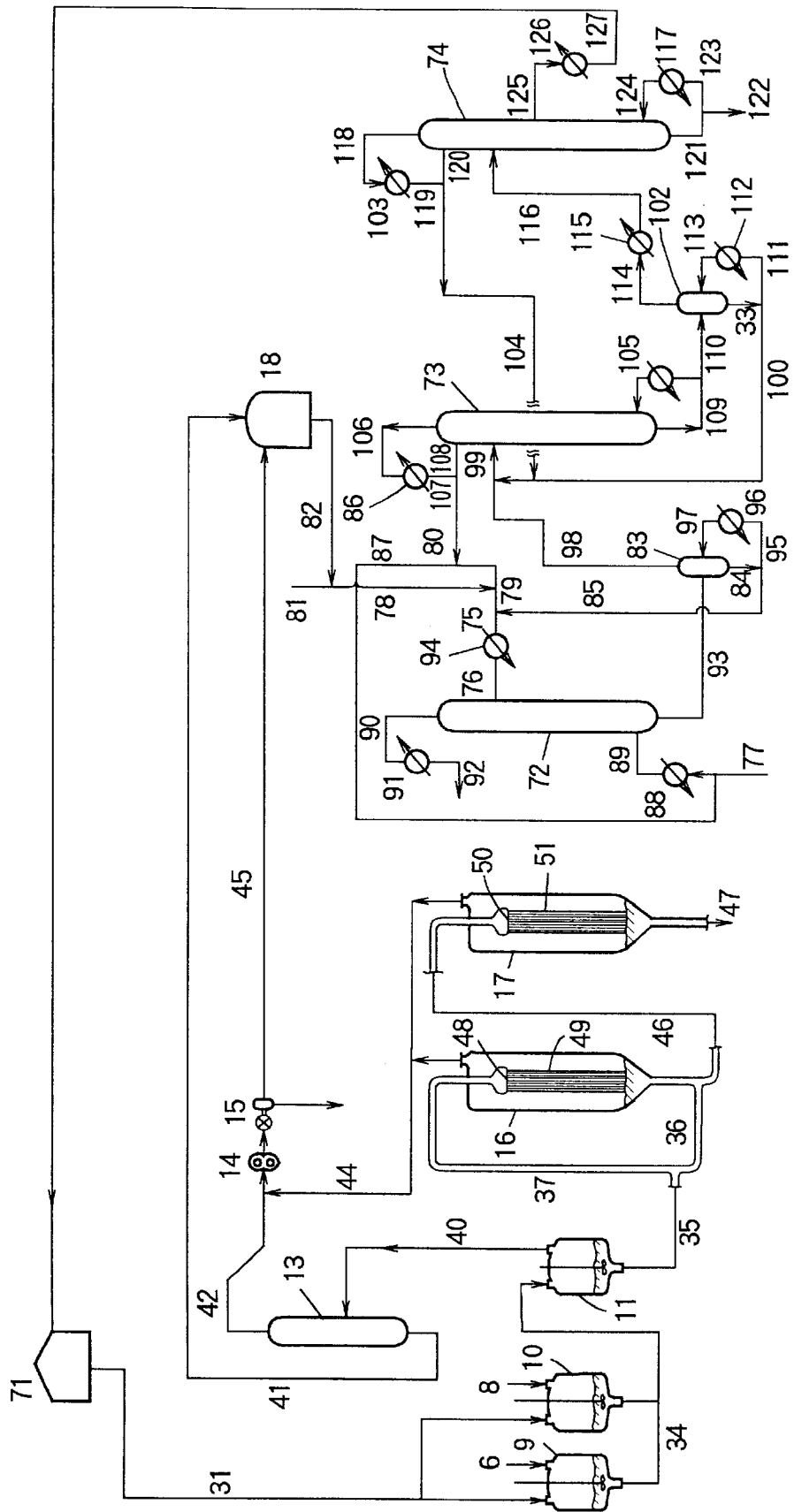
FIG. 4 is a diagram showing the system used in Comparative Example 1 for producing an aromatic polycarbonate.

An aromatic polycarbonate was produced in accordance with a system as shown in FIG. 4. The system of FIG. 4 comprises (i) production of diphenyl carbonate by a first stage and a second stage reactive distillation (conducted using continuous multi-stage distillation columns 72 and 73, respectively), and (ii) production of an aromatic polycarbonate while recovering a crude phenol product which is produced as a by-product and recycled to the above-mentioned continuous multi-stage distillation column 72 through crude phenol product accumulation tank 18. The above-mentioned production of an aromatic polycarbonate (ii) comprises a first stage and a second stage agitation polymerization (conducted using first stage agitation type polymerizer vessels 9 and 10 and second stage agitation type polymerizer vessel 11, respectively), a free-fall polymerization (conducted using free-fall polymerizer 16), and a wire-wetting fall polymerization (conducted using wire-wetting fall polymerizer 17).

<Aromatic polycarbonate production>

An aromatic polycarbonate was produced in substantially the same manner as in Example 1, except that bisphenol A was batchwise charged into first stage agitation type polymerizer vessels 9 and 10 through inlets 6 and 8, respectively and that diphenyl carbonate, which was produced in the diphenyl carbonate production stage described below, was batchwise charged into first stage agitation type polymerizer vessels 9 and 10 from diphenyl carbonate accumulation tank 71 through conduit 31.

<Diphenyl carbonate production>

A mixture of 20 kg of phenol and 4 kg of lead monoxide was heated to and maintained at 180° C. for 10 hours, thereby performing a reaction. After that period of time, water formed and contained in the resultant reaction mixture was distilled off together with unreacted phenol, to thereby obtain a lead catalyst.

At the initial stage of the operation, a mixture of fresh phenol having a purity of 99.97%, fresh dimethyl carbonate and the above-mentioned lead catalyst was fed from an inlet provided on conduit 75 (not shown) to first continuous multi-stage distillation column 72 (comprised of a plate column having a height of 6 m and equipped with 20 sieve trays) at a position of 0.5 m below the top thereof at a flow rate of 23.8 kg/hr through conduit 76, thereby allowing the mixture to flow down inside multi-stage distillation column 72 so as to perform a reaction. The composition of the mixture fed from conduit 76 during the initial stage of the operation was as follows: fresh dimethyl carbonate: 54.6% by weight; fresh phenol: 44.6% by weight; and lead catalyst: 0.43% by weight, in terms of the Pb concentration in the mixture. Further, fresh dimethyl carbonate was fed at a flow rate of 42.2 kg/hr from conduit 77 to the bottom of first continuous multi-stage distillation column 72. When the feeding of liquids recycled through conduits 78, 79 and 85 to conduit 75 was started, the feeding of the mixture from the inlet provided on conduit 75 was stopped. Subsequently, fresh phenol (which is the same phenol as the above-mentioned fresh phenol) was fed from conduit 81 to conduit 78 at a flow rate of 3.45 kg/hr.

After the operation reached a steady state, the mixture in conduit 76 had the following composition: phenol: 44.6% by weight; dimethyl carbonate: 49.8% by weight; methyl phenyl carbonate: 4.8% by weight; and lead catalyst: 0.43% by weight, in terms of the Pb concentration of the mixture {the mixture in conduit 76 was comprised of a liquid introduced from conduit 78 (i.e., a mixture of the fresh phenol and the by-product phenol), a liquid recycled from second continuous multi-stage distillation column 73 through conduits 80 and 79, and a liquid recycled from evaporator 83 through conduits 84 and 85}. The sample of the mixture in conduit 76 was taken from the sampling nozzle (not shown) provided on conduit 75, and subjected to the determination of the content of each of phenol, dimethyl carbonate and methyl phenyl carbonate and the purity of the phenol in the mixture. The content of each of phenol, dimethyl carbonate and methyl phenyl carbonate in the above mixture, and the purity of the phenol in the mixture were measured by high performance liquid chromatography (SCL-6B, manufactured and sold by Shimadzu Corporation, Japan). The content of the lead catalyst in the above mixture was measured by an ICP (inductively coupled plasma emission spectral analyzer), using JY38PII (manufactured and sold by Seiko Electronics Co., Ltd., Japan).

First continuous multi-stage distillation column 72 was operated under conditions wherein the temperature at the column bottom was 203° C., the pressure at the column top was 6.5 kg/cm$^2$-G, and the reflux ratio was 0.

In first continuous multi-stage distillation column 72, a heat necessary for performing the reaction and distillation was supplied from a mixture of the fresh dimethyl carbonate fed from conduit 77 and a portion of a low boiling point reaction mixture containing unreacted dimethyl carbonate withdrawn from the top of second continuous multi-stage distillation column 73 and recycled through condenser 86 and conduits 80 and 87, which mixture was heated in evaporator 88.

Gas distilled from the top of first continuous multi-stage distillation column 72 was led into condenser 91 through conduit 90, in which the gas was condensed. A low boiling point reaction mixture containing by-produced methanol was continuously withdrawn from conduit 92 at a flow rate of 42.3 kg/hr.

A reaction mixture was continuously withdrawn from the bottom of first continuous multi-stage distillation column 72 at a flow rate of 23.6 kg/hr and led into first evaporator 83 through conduit 93. In first evaporator 33, an evaporation-concentrated liquid containing the lead catalyst was formed. A portion of the concentrated liquid was led into preheater 94 through conduits 84, 85 and 75 and recycled to first continuous multi-stage distillation column 72 through conduit 76. The remainder of the concentrated liquid was recycled to first evaporator 83 through conduit 95, reboiler 96 and conduit 97.

An evaporated gas containing methyl phenyl carbonate withdrawn from first evaporator 83 through conduit 98 at a flow rate of 22.3 kg/hr was continuously fed through conduit 99 to second continuous multi-stage distillation column 73 (a column having a height of 6 m, which is comprised of a plate column equipped with 20 sieve trays) at a position 1.5 m below the top thereof, in which most of the methyl phenyl carbonate fed to second continuous multi-stage distillation column 73 was allowed to flow down in liquid form inside second continuous multi-stage distillation column 73, thereby performing a reaction in the presence of the above-mentioned lead catalyst which was fed to second continuous multi-stage distillation column 73 from a nozzle (not shown) provided on conduit 100 through conduits 101 and 99. The lead catalyst was used in an amount such that the Pb concentration of a mixture in conduit 99 was maintained at 0.8% by weight. After the operation reached a steady state, the mixture in conduit 99 was fed to second continuous multi-stage distillation column 73 at a flow rate of 23.6 kg/hr. The composition of the mixture in conduit 99 was as follows: dimethyl carbonate: 43.1% by weight; phenol 24.5% by weight; methyl phenyl carbonate: 27.1% by weight; and lead catalyst: 0.80% by weight, in terms of the Pb concentration of the mixture in conduit 99. The above-mentioned mixture in conduit 99 was comprised of the evaporated gas containing methyl phenyl carbonate fed from conduit 98, an evaporation-concentrated liquid formed in second evaporator 102 and withdrawn through conduit 100, and a liquid fed through conduit 104 which was formed by the condensation in condenser 103 of a gas distilled from purification column 74 for diphenyl carbonate.

Second continuous multi-stage distillation column 73 was operated under conditions wherein the temperature at the column bottom was 198° C., the pressure at the column top was 280 mmHg, and the reflux ratio was 1.5. A heat necessary for performing the reaction and distillation was supplied from a column bottom liquid heated by means of reboiler 105.

A gaseous low boiling point reaction mixture containing dimethyl carbonate, which was distilled from the top of second continuous multi-stage distillation column 73, was led into condenser 86 through conduit 106, in which the gaseous mixture was condensed. A portion of the resultant condensate was refluxed to second continuous multi-stage distillation column 73 through conduits 107 and 108. The remainder of the condensate in condenser 86 was continuously withdrawn through conduits 107 and 80, and recycled to first continuous multi-stage distillation column 72 through preheater 94 and conduit 76. A portion of the condensate in conduit 80 was recycled to the lower portion of first continuous multi-stage distillation column 72 through conduit 87, evaporator 88 and conduit 89. A high boiling point reaction mixture containing the catalyst and diphenyl carbonate was continuously withdrawn from the bottom of second continuous multi-stage distillation column 73 and led into second evaporator 102 through conduits 109 and 110. In second evaporator 102, an evaporation-concentrated liquid containing the lead catalyst was formed. A portion of the concentrated liquid was recycled to second evaporator 102 through conduit 111, reboiler 112 and conduit 113. The remainder of the concentrated liquid withdrawn was recycled to second continuous multi-stage distillation column 73 through conduits 33, 100 and 101. On the other hand, an evaporated gas (having a diphenyl carbonate content of 98.3% by weight) formed in second evaporator 102 was led into condenser 115 at a flow rate of 4 kg/hr through conduit 114, in which the gas was condensed. The resultant condensate was fed into purification column 74 for diphenyl carbonate through conduit 116. In purification column 74, a heat necessary for conducting distillation was supplied from the column bottom liquid heated by means of reboiler 117. A gaseous low boiling point mixture containing phenol and methyl phenyl carbonate distilled from the top of purification column 74 was led through conduit 118 into condenser 103, in which the gas was condensed. A portion of the resultant condensate was recycled to purification column 74 through conduits 119 and 120. The remainder of the condensate was recycled to second continuous multi-stage distillation column 73 through conduits 119, 104, 101 and 99. A portion of the reaction mixture at the bottom of purification column 74 was withdrawn through conduits 121 and 122, and the remainder of the reaction mixture was recycled to the column bottom through conduits 121, 123, reboiler 117 and conduit 124. Purified diphenyl carbonate was withdrawn from purification column 74 at a middle portion thereof and led at a flow rate of 3.9 kg/hr through conduit 125, condenser 126 and conduit 127 to accumulation tank 71 for purified diphenyl carbonate.

The above-mentioned operation was continued until a crude phenol product, which was by-produced in the aromatic polycarbonate production stage, was stored in crude phenol product accumulation tank 18. Then, the phenol fed to first continuous multi-stage distillation column 72 was changed to phenol recovered from the polymerization system of the aromatic polycarbonate production stage. At this point of time, the purity of phenol in the crude phenol product was 91% by weight. The crude phenol product stored in accumulation tank 18 for crude phenol product (i.e., the by-produced phenol recovered from the polymerization system of the system of FIG. 4) was fed to conduit 78 through conduit 82 at a flow rate of 3.3 kg/hr, and the flow rate of the fresh phenol at this point of time was lowered to 0.15 kg/hr. The content of the crude phenol product in the liquid in conduit 78 was 96% by weight. 15 minutes after the change of the phenol (fed to first continuous multi-stage distillation column 72) to the crude phenol product, the result of the reaction in first continuous multi-stage distillation column 72 began to become poor. Further, 2 hours after the change of the phenol (fed to first continuous multi-stage distillation column 72) to the crude phenol product, the operation of the diphenyl carbonate production became impossible.

The determination of the concentration of the lead catalyst in the liquid taken from the sampling nozzle provided on conduit 75 showed that the concentration of the lead catalyst was lowered to 5.3% by weight. Therefore, the reaction was stopped and first continuous multi-stage distillation column 72 was examined. As a result, it was found that the deposition of the lead catalyst occurred at a portion in first continuous multi-stage distillation column 72 which is close to the plate connected to conduit 76.

Comparative Example 2

Figure 5:
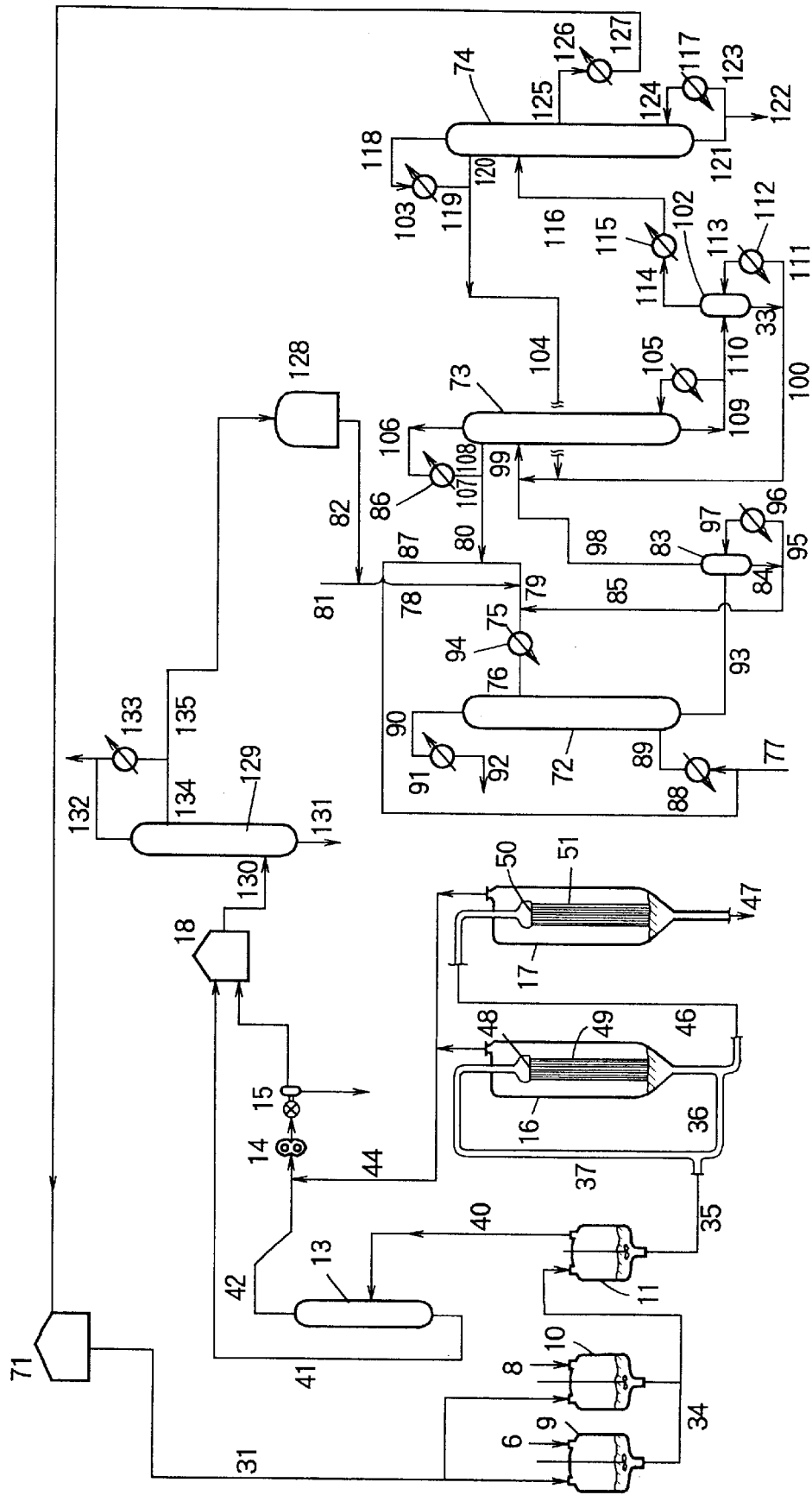
FIG. 5 is a diagram showing the system used in Comparative Example 2 for producing an aromatic polycarbonate.

An aromatic polycarbonate was produced in accordance with a system as shown in FIG. 5. The system of FIG. 5 comprises (i) production of diphenyl carbonate by a first stage and a second stage reactive distillation (conducted using continuous multi-stage distillation columns 72 and 73, respectively), and (ii) production of an aromatic polycarbonate while recovering a crude phenol product which is produced as a by-product, wherein the crude phenol product is purified by distillation to thereby obtain a purified phenol and the obtained purified phenol is recycled to the above-mentioned continuous multi-stage distillation column 72 through purified phenol accumulation tank 128. The above-mentioned production of an aromatic polycarbonate (ii) comprises a first stage and a second stage agitation polymerization {conducted using first stage agitation type polymerizer vessels 9 and 10 and second stage agitation type polymerizer vessel 11, respectively}, a free-fall polymerization (conducted using free-fall polymerizer 16), and a wire-wetting fall polymerization (conducted using wire-wetting fall polymerizer 17).

Substantially the same operation as in Comparative Example 1 was repeated, except that the crude phenol product recovered from the aromatic polycarbonate production stage was purified using phenol purification column 129 to thereby obtain a purified phenol, and that the obtained purified phenol was supplied to the diphenyl carbonate production stage.

The crude phenol product recovered from the aromatic polycarbonate production stage was stored in crude phenol product accumulation tank 18 and fed to phenol purification column 129 through conduit 78, wherein the internal pressure and internal temperature of phenol purification column 129 were 350 torr and 160° C., respectively. Diphenyl carbonate, bisphenol A and an aromatic polycarbonate oligomer were withdrawn from the bottom of phenol purification column 129 through conduit 131. Phenol containing light low-boiling point components (such as water) was withdrawn from the top of phenol purification column 129 and fed to condenser 133 through conduit 132. The light low-boiling point components were separated from the gaseous phase in condenser 133 and distilled. On the other hand, phenol was separated from the light low-boiling point components, using condenser 133 to thereby obtain a purified phenol. A part of the obtained purified phenol was recycled to phenol purification column 129 through conduit 134, and the remainder of the purified phenol was led to purified phenol accumulation tank 128. The purity of phenol in purified phenol accumulation tank 128 was 99.98% by weight. The amount of the light low-boiling point components (separated from the gaseous phase in condenser 133 and distilled) was small. However, the components withdrawn from the bottom of phenol purification column 129 was colored light yellow and therefore, cannot be recycled to the polymerization system. Thus, those components were incinerated. The total amount of the incinerated components was as large as about 4% by weight, based on the total weight of the materials fed to the system of FIG. 5. That is, large amounts of the materials were lost and the yield of the aromatic polycarbonate was lowered.

After the operation of the diphenyl carbonate production reached a steady state, phenol used as a phenol material was changed to the purified phenol, which was obtained by purifying the crude phenol product recovered from the aromatic polycarbonate production stage. The operation of the diphenyl carbonate production could be continued without causing any problem.

The obtained aromatic polycarbonate had a weight average molecular weight of 27,800. Further, it was found that the b*-value of the aromatic polycarbonate was 3.5.

Example 2

Figure 6:
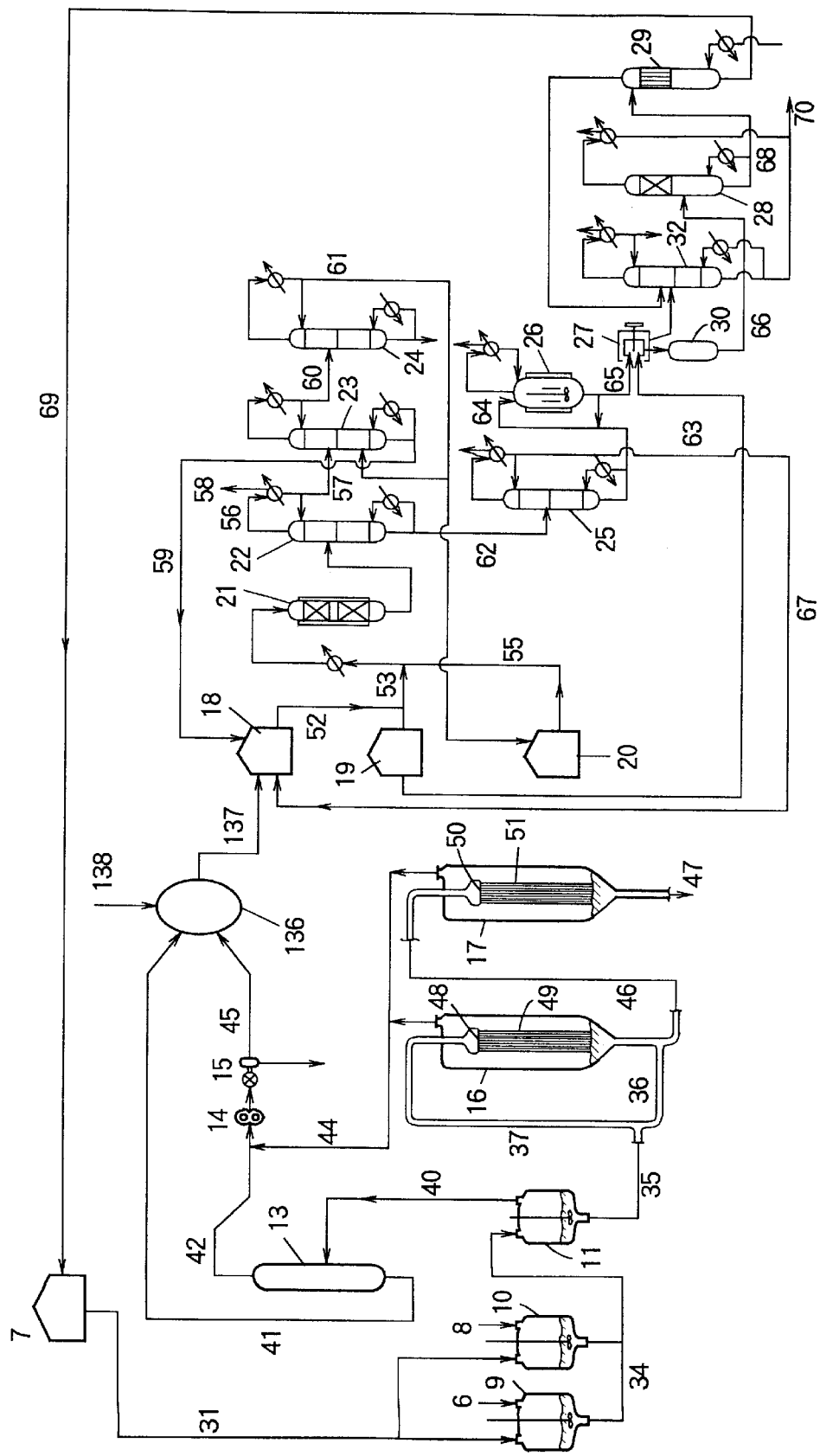
FIG. 6 is a diagram showing the system used in Example 2 for producing an aromatic polycarbonate.

An aromatic polycarbonate was produced in accordance with a system as shown in FIG. 6. Substantially the same operation as in Example 1 was repeated, except that hydrolysis chamber 136 was provided, wherein phenol condenser 13 was connected to hydrolysis chamber 136 through conduit 41, liquid seal-type vacuum pump 15 was connected to hydrolysis chamber 136 through conduit 45, and hydrolysis chamber 136 was connected to crude phenol product accumulation tank 18 through conduit 137.

The crude phenol product recovered from the polymerization system of the aromatic polycarbonate production stage was fed to hydrolysis chamber 136 through conduits 41 and 45. Water was fed to hydrolysis chamber 136 through conduit 138 so that the amount of water became 1% by weight, based on the weight of the crude phenol product. Hydrolysis chamber 136 was operated under conditions wherein the temperature was 150° C. and the residence time was about 2 hours. The crude phenol product treated in hydrolysis chamber 136 was led to crude phenol product accumulation tank 18 through conduit 137.

The above operation using the system of FIG. 6 was continuously carried out for 800 hours to produce bisphenol A and an aromatic polycarbonate. Bisphenol A obtained 800 hours after the start of the operation contained phenol and a chroman compound, but the contents thereof were as low as 40 ppm and 98 ppm, respectively. Further, the APHA value of bisphenol A obtained 800 hours after the start of the operation was as low as 5.

As apparent from the above, the use of the crude phenol product has no harmful effects. Further, no waste occurred in the recovery of the crude phenol product from the polymerization system for producing the aromatic polycarbonate.

The obtained aromatic polycarbonate had a weight average molecular weight of 27,800. Further, it was found that the b*-value of the aromatic polycarbonate was 3.3, showing that the quality of the obtained aromatic polycarbonate was very high.

Example 3

Figure 7:
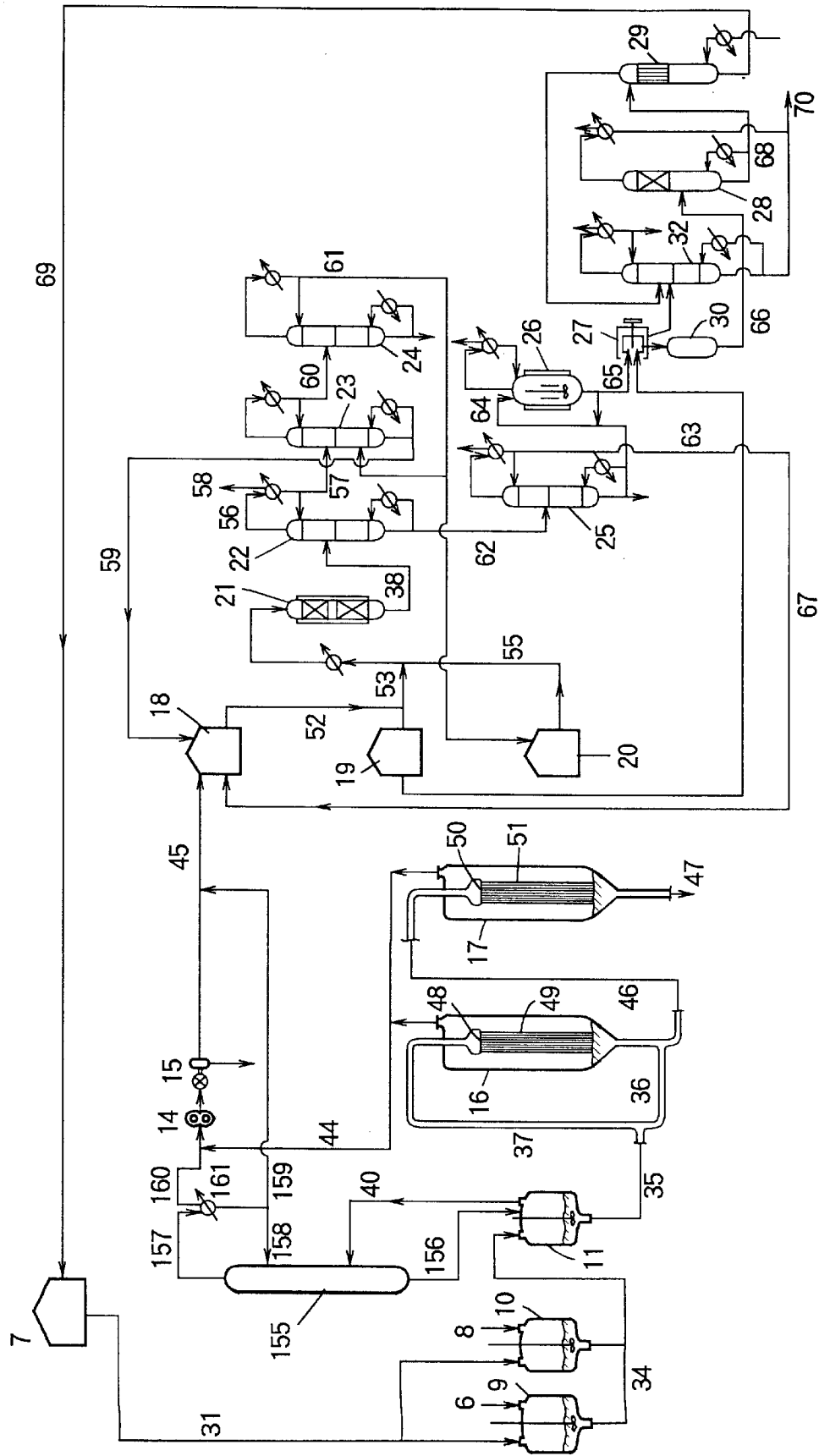
FIG. 7 is a diagram showing the system used in Example 3 for producing an aromatic polycarbonate.

An aromatic polycarbonate was produced in accordance with a system as shown in FIG. 7. Substantially the same operation as in Example 1 was repeated, except that crude phenol product withdrawn from second stage agitation type polymerizer vessel 11 was fed to diphenyl carbonate recovering column 155 so that diphenyl carbonate, bisphenol A and an aromatic polycarbonate oligomer were separated from phenol and recycled to the polymerization step.

The liquid obtained from the bottom of diphenyl carbonate recovering column 155, which contains diphenyl carbonate, bisphenol A and an aromatic polycarbonate oligomer as major components, was recycled to second stage agitation type polymerizer vessel 11 through conduit 156. An evaporated gas distilled from the top of diphenyl carbonate recovering column 155 was fed to condenser 161 and condensed so as to generate a gaseous phase and a liquid phase. The liquid phase was led to crude phenol product accumulation tank 18 through conduits 159 and 45. The gaseous phase was led to roots blower 14 through conduit 160, led to liquid seal-type vacuum pump 15 and led to crude phenol product accumulation tank 18 through conduit 45. The purity of phenol in crude phenol product accumulation tank 18 was 98.5% by weight.

The above operation using the system of FIG. 7 was continuously carried out for 800 hours to obtain an aromatic polycarbonate. Bisphenol A obtained 800 hours after the start of the operation contained phenol and a chroman compound, but the contents thereof were as low as 43 ppm and 95 ppm, respectively. Further, the APHA value of bisphenol A obtained 800 hours after the start of the operation was as low as 5.

As apparent from the above, the use of the crude phenol product has no harmful effects. Further, no waste occurred in the recovery of the crude phenol product from the polymerization system for producing the aromatic polycarbonate.

The obtained aromatic polycarbonate had a weight average molecular weight of 28,300. Further, it was found that the b*-value of the aromatic polycarbonate was 3.4, showing that the quality of the obtained aromatic polycarbonate was very high.

INDUSTRIAL APPLICABILITY

According to the method of the present invention, a crude phenol product is recovered from a polymerizer for producing an aromatic polycarbonate, and the recovered crude phenol product as such, containing a by-product phenol as a main component and containing impurities, can be utilized for producing bisphenol A, finally for producing an aromatic polycarbonate, without any purification or the like. In the method of the present invention, not only can a necessity for complicated operations, such as a purification treatment, be reduced, but also the amount of wastes can be reduced and the yield of the aromatic polycarbonate, based on any of phenol and bisphenol A, can be improved. Therefore, the method of the present invention is extremely advantageous from the commercial view-point.

What is claimed is:

1. A method for producing an aromatic polycarbonate, which comprises:

feeding acetone and a phenol material to a reactor to effect a reaction between said acetone and said phenol material, thereby producing bisphenol A, and polymerizing said bisphenol A with diphenyl carbonate in a polymerizer to produce an aromatic polycarbonate while producing phenol as a by-product, wherein said by-product phenol is recovered from said polymerizer as a crude phenol product containing said by-product phenol as a main component and containing impurities, and said crude phenol product is used as at least a part of said phenol material for producing bisphenol A.

2. The method according to claim 1, wherein said crude phenol product has a purity of 50 to 99% by weight in terms of the phenol content thereof.

3. The method according to claim 1 or 2, wherein, before said crude phenol product is used for producing bisphenol A, said crude phenol product is treated for the hydrolysis of said impurities contained therein.

4. The method according to claim 1 or 2, wherein said bisphenol A is obtained in the molten state, and the molten state of the bisphenol A is maintained until the bisphenol A is subjected to the polymerization thereof with the diphenyl carbonate.

5. The method according to claim 1 or 2, wherein said bisphenol A subjected to the polymerization thereof with the diphenyl carbonate is in the form of a phenol adduct thereof.

6. The method according to claim 1 or 2, wherein said phenol material comprises phenol and at least one impurity selected from the group consisting of o-cre-sol, methyl o-methoxybenzoate, phenyl salicylate, o-phenoxybenzoic acid, phenyl o-phenoxybenzoate, phenyl tolyl carbonate, xanthone, a catechol derivative, diphenyl carbonate, bisphenol A and an aromatic polycarbonate oligomer.

* * * * *

UNITED STATES PATENT AND TRADEMARK OFFICE
CERTIFICATE OF CORRECTION

PATENT NO. : 6,277,945 B1
DATED : August 21, 2001
INVENTOR(S) : Hiroshi Hachiya and Kyosuke Komiya It is certified that error appears in the above-identified patent and that said Letters Patent is hereby corrected as shown below:

<u>Title page,</u>
Item [73], please amend from "Asahi Kasei Kogyo Kabushiki Kaisha" to
-- Asahi Kasei Kabushiki Kaisha --.

Signed and Sealed this

Second Day of July, 2002

Attest:

JAMES E. ROGAN
*Attesting Officer*   *Director of the United States Patent and Trademark Office*